United States Patent [19]

Hellouin de Menibus

[11] 4,289,018
[45] Sep. 15, 1981

[54] METHOD AND APPARATUS FOR MEASURING DEGASIFICATION

[75] Inventor: Olivier Hellouin de Menibus, Etampes, France

[73] Assignee: AMS, S.A., Fresnes, France

[21] Appl. No.: 67,113

[22] Filed: Aug. 16, 1979

[51] Int. Cl.³ .............................................. G01N 7/14
[52] U.S. Cl. ..................................... 73/19; 73/61 R; 73/861.04
[58] Field of Search .................... 73/19, 846.04, 168; 55/168, 169; 73/61 R

[56] References Cited

U.S. PATENT DOCUMENTS

| | | | |
|---|---|---|---|
| 2,745,282 | 5/1956 | Rochon | 73/19 X |
| 3,150,516 | 9/1964 | Linnenbom et al. | 73/19 |
| 3,748,898 | 7/1973 | de Menibus | 73/168 |
| 3,905,222 | 9/1975 | Boillet | 73/19 |
| 3,964,864 | 6/1976 | Dahms | 73/19 X |
| 4,184,359 | 1/1980 | Gracey | 73/19 |

FOREIGN PATENT DOCUMENTS 2221551  5/1972  Fed. Rep. of Germany .......... 73/19

Primary Examiner—Daniel M. Yasich
Attorney, Agent, or Firm—Sandler & Greenblum

[57] ABSTRACT

A method is provided for measuring the amount of gas in a liquid system which comprises a tank and a vacuum pump. The method includes the steps of operating a vacuum pump to exert a predetermined vacuum upon the liquid in order to desolubilize gas from the liquid and then separating the desolubilized gas from the liquid. The flow rate of the separated gas is measured by a flow meter and the amount of gas remaining in the liquid is determined as a function of this measurement and displayed by the flow meter. Gas measurement apparatus is provided for use with a liquid system and comprises a tank, a vacuum pump and a flow meter. This apparatus can be used in combination with an auxiliary hydraulic circuit adapted for use as part of a test bench for performing tests on a primary hydraulic circuit.

7 Claims, 2 Drawing Figures

METHOD AND APPARATUS FOR MEASURING DEGASIFICATION

BACKGROUND OF THE INVENTION

1. Field of the Invention

The invention relates to the regulation and control of degasification of a hydraulic circuit.

2. Description of Prior Art

Hydraulic circuits generally require a liquid which is void of any dissolved or suspended gases. In effect, gases in suspension, particularly air, result in disturbances in the operation of the system, such as cavitation in the pumps, pressure jumps, defects in regulation, strange noises, etc. Entrapped gas even results in serious deterioration of the elements in the circuit, e.g., erosion by virtue of cavitation, corrosion resulting from the abrasion of materials etc. The dissolved gases can become liberated during storage or in the course of the liquid being heated. Finally, the gases may concentrate in a pocket at certain high points of the circuit thus introducing an impedance within the circuit. Thus, it is often necessary or at least desirable to periodically degas the liquid circulating through a hydraulic circuit.

Degasification becomes indispensible when considering hydraulic circuits used in airplanes for reasons of safety. First, these circuits comprise components which are very sensitive to an absence of homogeneity in the liquid. Furthermore, in modern airplanes, the two tank stages (high and low pressure) are entirely closed and air, leaking in very small quantities but in a continuous stream, enters through the connections and the safety joints and cannot be separated from the oil in the tank as partially occurs in conventional tanks where gas exists above the level of the liquid. Finally, the response times of elements controlled by the circuit are directly influenced by the impedance of the circuit and must remain within precise limits.

The degasification of the hydraulic circuit of airplanes is normally performed at the same time as its purification and its testing which are performed by means of a test bench. The test bench comprises an auxiliary hydraulic circuit comprising essentially one pump, filters, and a relatively large volume tank, and is connected in parallel across the circuit being checked. The pump of the auxiliary circuit is provided with its own driving means. The oil of the circuit to be checked passes permanently through the tank of the auxiliary circuit and the degasification is performed by connecting the high point of the tank of the auxiliary circuit to a vacuum pump and involves both the circuit being checked and the auxiliary circuit. In other words, such degasification occurs exactly in the manner of a simple hydraulic circuit with a conventional reservoir.

It is always important to known whether the degasification is operating adequately or not. In the case of a permanent degasification of a simple circuit one can appropriately vary the degree of vacuum created in the tank by the vacuum pump. In the case of a periodic degasification on a test bench with an auxiliary circuit, one thus determines the moment when the operation may be stopped.

Presently, in order to verify that the quantity of gas contained in the liquid is sufficiently low, one inserts into the return line of the tank a transparent area which is appropriately lit and which serves as a viewer. The oil which circulates in the vicinity of the viewer has a relatively low pressure and one can evaluate the density by virtue of the number of bubbles of visible gas contained in the oil. The operator evaluates whether the fluid has been degassed by evaluating the number of bubbles which are visible to him and determines whether they are below a certain volume. It is clear that this method of verification can be only qualitative and subjective because the bubbles are generally very small, very numerous and in rapid movement. Furthermore, dissolved gases pass without being seen while the proportion between the dissolved gas and the suspended gas varies as a function of temperature. Pressure in the viewer will exert a strong effect and cannot be maintained perfectly constant.

SUMMARY OF THE INVENTION

It is, therefore, an object of the invention to provide an accurate technique for measuring the gas content of liquids in hydraulic circuits and the like.

It is a further object of the invention to provide an accurate technique which may be either manual or automatic and which accurately indicates the amount of gas contained within a liquid.

These and other objects are fulfilled by means of the method of the invention for measuring the amount of gas in a liquid system which comprises a tank and a vacuum pump. The method comprises the steps of operating the vacuum pump to exert a predetermined level of suction over the liquid so as to desolubilize gas from the liquid and then separating the desolubilized gas which has left the liquid. The flow rate of separated gas is then measured and this measurement will serve to indicate the amount of gas within the liquid itself.

In a preferred embodiment of the invention, the temperature of the liquid is maintained within two predetermined points such that the flow rate of gas removed from the system can be used as an accurate measurement for indicating the amount of gas in the liquid at that time.

In a most preferred embodiment of the invention the flow rate of gas being separated from the liquid is measured by a flowmeter. The flowmeter may assume any form although two preferred forms are set forth in the attached drawings. In the first, a flowmeter is illustrated having a flexible pointer which is deflected by the gas flow. A protrusion or the like is positioned along the pointer and this protrusion serves to interfere with an excitation ray emitted by a photocell. By cutting off this ray a signal may be generated for purposes of either automatically or manually adjusting the degasification procedure to take the reduced gas flow rate into account. In an alternative embodiment, the flowmeter may comprise a float within a tube. The float is moved as a function of the gas flowrate flowing through the tube, such a system being useful for visually indicating the extent of gas flow rate through the tube. The outside of the tube may be provided with graduations which directly indicate the amount of gas in the liquid, based upon the height of the pointer (after having been calibrated to take into account temperature, etc.).

Furthermore, the above objectives are fulfilled by means of the gas measurement apparatus of the invention which is adapted for use with a liquid circuit. The apparatus comprises a tank adapted to receive the liquid and a vacuum pump. The vacuum pump is connected to the tank whereby dissolved gas in the liquid is desolubilized under the vacuum exerted by the pump. A flow meter is provided which is adapted to measure the flow rate of gas desolubilized from the liquid.

In a preferred embodiment of the invention, the gas measurement apparatus may further comprise a vacuum regulator adapted to regulate the amount of vacuum exerted by the pump on the fluid.

A gas-liquid separator may be interposed between the tank and the flow meter for purposes of separating the desolubilized gas from the liquid. The vacuum pump is preferably connected to a high point in the tank.

Once again, the flow meter used may preferably be either a float and tube flow meter or a flow meter of the pointer type.

As yet another aspect of the invention, the apparatus may be attached to an auxiliary circuit in a test bench adapted to be used to measure the gas content of a liquid in a hydraulic circuit. One again, the apparatus comprises a tank, a vacuum pump, a vacuum regulator, and a flowmeter.

Thus, according to the invention, it is possible to accurately measure the amount of gas remaining within a liquid as a function of the amount of gas being removed.

DESCRIPTION OF PREFERRED EMBODIMENTS

The invention provides certain and highly objective means for quantitatively evaluating the percentage of gas remaining in the liquid. The invention is based on the fact that the quantity of gas extracted per unit time is a function of the total percentage of the gas (dissolved or in suspension) contained in the liquid, all other factors being equal (temperature, vauum, free surface of the liquid, i.e., cross-sectional area of the tank).

According to the invention, the degree of degasification is measured by measuring the flow meter of gas in liquid extracted from the tank.

For a given installation, with a given tank, in which the operation, for example a test bench for a hydraulic circuit, takes place under predetermined conditions of temperature and pressure, it is possible to utilize a flow meter which is directly graduated with respect to the percentage of gas contained in the liquid. Such a flow meter may be of the tube and float type. It is further possible to provide a flow meter having a flexible strip, pointer or tongue and a photoelectric cell which makes it possible to automatically stop the degasification operation when the percentage of gas remaining reaches a predetermined threshhold, or to warn the operator by a visible electric indicator or a cell alarm.

The invention further relates to a test bench for a hydraulic circuit comprising a degasification system which carries out the above method.

Figure 1:
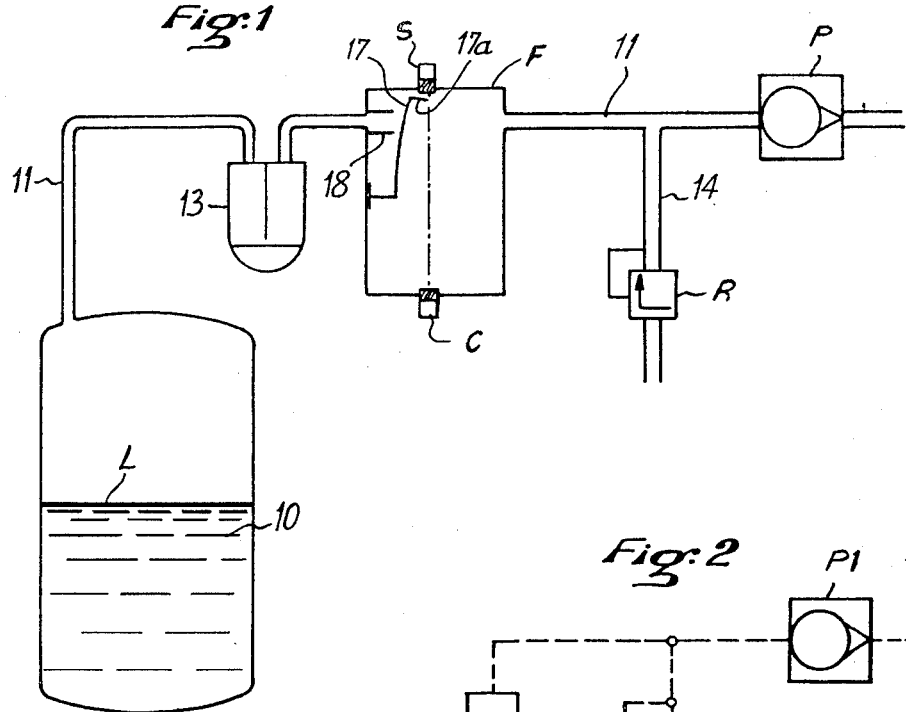
FIG. 1 is schematic diagram of a degasification verification system having a flexible pointer.

In FIG. 1, a hydraulic circuit, not shown, comprises a tank 10 containing liquid having a level whose high point is connected by a line 11 to a vacuum pump P. In a known fashion, in the line 11, is interposed an oil-water separator 13 for the recovery of the oil entrained in the aspirated air and is tapped by a shunt line 14 going to a vacuum regulator R which regulates vacuum pump P to control in a conventional manner the value of the vacuum which must be maintained by pump P. Between the separator 13 and the attachment of the regulator 15 is arranged a flow meter F comprising a flexible strip, tongue or pointer 17 situated facing the inlet nozzle 18 of the gas into flowmeter. Thus, the amplitude of the flexion of the strip or pointer 17 is a function of the flow rate of the gas. At its upper free end, the pointer or strip 17 comprises a protrusion, baffle or flange 17a which, for a sufficient flexion of the strip forms a baffle between a source S and a photoelectric cell C. The apparatus is set such that for a sufficiently low flow, corresponding to insufficient degasification, the baffle 17a disengages from the path of the excitation ray of the cell C and this latter thus initiates the stoppage of the pump P or any other procedure for carrying on the tests. Of course, the flow meter F 16 having a strip may be replaced by any type of flow meter, such as for example a tube and float flow meter, and the control of the pump P can be entirely manual.

Figure 2:
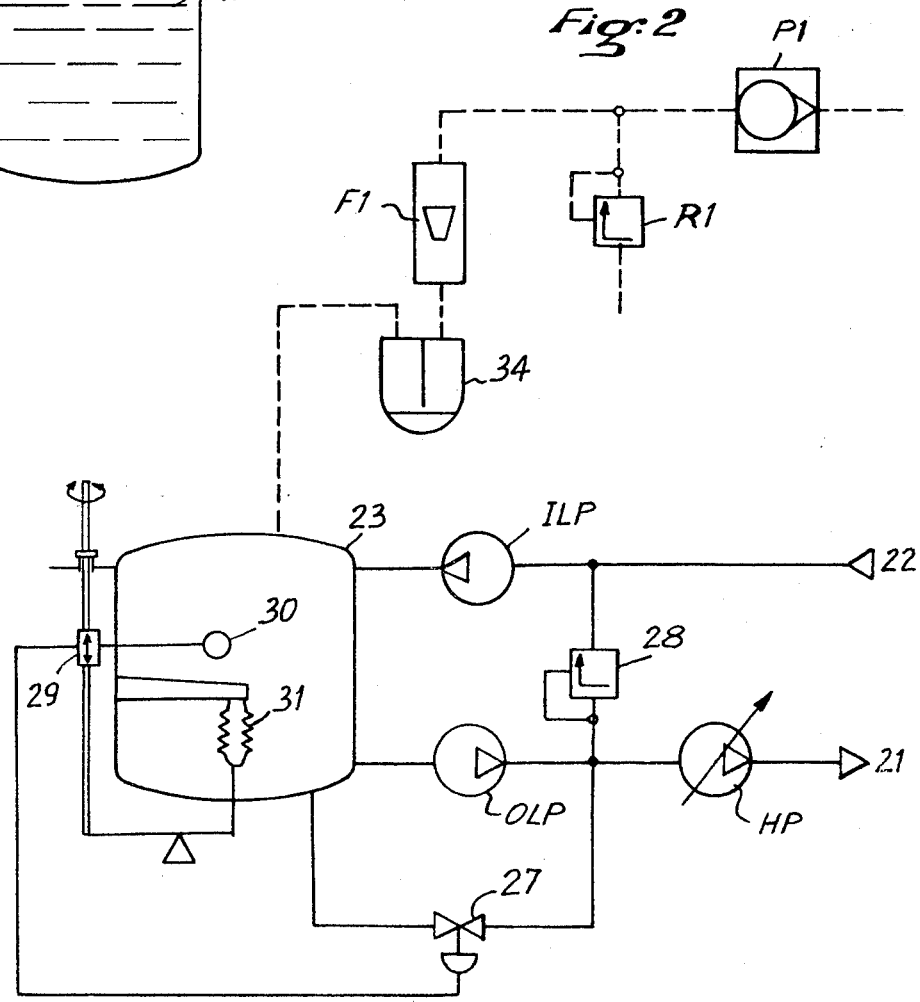
FIG. 2 schematically illustrates a test bench for a hydraulic circuit with a level regulator having thermal compensation and degasification verification by a tubular flow meter.

FIG. 2 schematically illustrates, in solid lines, the hydraulic circuit of a test bench adapted to be attached in parallel across a pump (not shown) of a hydraulic circuit to be tested, thereby acting as an auxiliary hydraulic circuit. Such an auxiliary circuit with its points of attachment 21 and 22, its tank 23, its high pressure pump H P having a variable flow rate, its low pressure constant flow rate intake pump ILP and output pump OLP, its controlled pneumatic gate valve 27 and its recycle valve 28 is presently well known; its function being described in a detailed fashion in U.S. Pat. No. 3,748,898 in the name of the applicant, the disclosure of which is incorporated herein. The tank 23 is equipped with a level sensor 29 having a float 30 and a temperature compensator 31, as is described in the above U.S. patent. To this known auxiliary circuit is connected a degasification circuit shown in dashed lines in the Figure which comprises a vacuum pump P1, a vacuum regulator R1, a separator 34, and as has been described above, a flow meter F1. In the example shown, the flow meter is of the tube and float type.

Although the invention has been described with respect to particular means and apparatus, it is to be understood that the invention is not limited to those means specifically disclosed but extends to all alternative and equivalent embodiments covered by the claims.

What is claimed is:

1. A method of measuring the amount of gas in a liquid system which comprises a tank and a vacuum pump, said method comprising the steps of:
   (a) maintaining the temperature of said system at a predetermined level;
   (b) operating said pump to exert a predetermined level of suction over said liquid to desolubilize gas from said liquid;
   (c) separating said desolubilized gas leaving said liquid from said liquid by a gas-liquid separator;
   (d) measuring the flow rate of said separated gas from said separator; and
   (e) determining the amount of gas remaining in said liquid as a function of said flow rate.

2. A gas measurement apparatus adapted to measure the amount of gas in a liquid system comprising:
   (a) a tank adapted to receive said liquid;
   (b) a vacuum pump fluidly connected by a line to a high point of said tank and adapted to desolubilize dissolved gas from said liquid under a vacuum exerted by said pump;

(c) a vacuum regulator adapted to regulate the amount of said vacuum exerted;

(d) a gas-liquid separator adapted to separate said desolubilized gas leaving said liquid from said liquid, said separator being interposed between said tank and a flow meter; and (e) said flow meter including means for measuring the flow rate of said gas and for determining the amount of gas remaining in said liquid as a function of said flow rate at any given time.

3. The gas measurement apparatus as defined by claim 2 wherein said flow meter is of the tube and float type.

4. The gas measurement apparatus as defined by claim 3 wherein said tube and flow meter is graduated in terms of a percentage of gas contained in liquid in order to provide a measurement of the amount of gas remaining in the liquid.

5. A gas measurement apparatus adapted to measure the amount of gas in a liquid system and comprising:

(a) a tank adapted to receive said liquid;

(b) a vacuum pump, said vacuum pump being fluidly connected by a line to a high point of said tank and being adapted to desolubilize dissolved gas from said liquid under a vacuum exerted by said pump;

(c) a vacuum regulator adapted to regulate the amount of said vacuum exerted;

(d) a gas-liquid separator adapted to separate said desolubilized gas leaving said liquid from said liquid, said separator interposed between said tank and a flow meter;

(e) said flow meter including means for measuring the flow rate of said desolubilized gas and means for determining the amount of gas remaining in said liquid as a function of said flow rate at any given time, said flow meter comprising a flexible pointer arranged within the flow path of said separated gas, said pointer including a protrusion at one end which is adapted to interrupt the excitation ray of a photoelectric cell.

6. The gas measurement apparatus as defined by claim 2 in combination with an auxiliary hydraulic circuit comprising a high pressure pump having a high variable flow rate, a low pressure constant flow rate intake pump and a low pressure constant flow rate output pump, a controlled pneumatic gate valve and a recycle valve, said tank including a level sensor having a float and a temperature compensator.

7. The gas measurement apparatus as defined in claim 6 wherein said flow meter comprises a flexible pointer arranged within the path of flow of said gas, said pointer including a protrusion at one end which is adapted to interrupt the excitation ray of a photoelectric cell.

* * * * *

UNITED STATES PATENT AND TRADEMARK OFFICE
CERTIFICATE OF CORRECTION

PATENT NO. : 4,289,018
DATED : September 15, 1981
INVENTOR(S) : Olivier HELLOUIN DE MENIBUS It is certified that error appears in the above—identified patent and that said Letters Patent is hereby corrected as shown below:

Column 2, line 42, "flowmeter" should be --flow meter--;
           line 44, "flowmeter" should be --flow meter--; and
           line 53, "flowmeter" should be --flow meter--.
Column 3, line 19, "flowmeter" should be --flow meter--;
           line 45, "flowmeter" should be --flow rate--; and
           line 64, --L-- should be inserted after "level".
Column 4, line 7, "flowmeter" should be --flow meter--; and
           line 18, "16" should be deleted.

Signed and Sealed this

Fifteenth Day of December 1981

[SEAL]

Attest:

GERALD J. MOSSINGHOFF

Attesting Officer     Commissioner of Patents and Trademarks